US010064792B2

(12) United States Patent
Schlossman et al.

(10) Patent No.: US 10,064,792 B2
(45) Date of Patent: Sep. 4, 2018

(54) HYBRID COATED COSMETIC POWDERS AND METHODS OF MAKING AND USING SAME

(75) Inventors: David Schlossman, Short Hills, NJ (US); Yun Shao, Piscataway, NJ (US)

(73) Assignee: KOBO PRODUCTS INC., Plainfield, NJ (US)

( * ) Notice: Subject to any disclaimer, the term of this patent is extended or adjusted under 35 U.S.C. 154(b) by 725 days.

(21) Appl. No.: 11/841,290

(22) Filed: Aug. 20, 2007

(65) Prior Publication Data
US 2008/0014233 A1    Jan. 17, 2008

Related U.S. Application Data

(62) Division of application No. 10/791,424, filed on Mar. 1, 2004, now abandoned.

(60) Provisional application No. 60/451,056, filed on Feb. 28, 2003, provisional application No. 60/472,527, filed on May 22, 2003.

(51) Int. Cl.
| | | |
|---|---|---|
| B05D 7/00 | (2006.01) | |
| A61K 8/11 | (2006.01) | |
| A61Q 1/02 | (2006.01) | |

(52) U.S. Cl.
CPC .............. *A61K 8/11* (2013.01); *A61Q 1/02* (2013.01); *A61K 2800/412* (2013.01)

(58) Field of Classification Search
CPC .................................. A61K 8/11; A61Q 1/02
USPC ........................................................ 427/222
See application file for complete search history.

(56) References Cited

U.S. PATENT DOCUMENTS

| | | | | |
|---|---|---|---|---|
| 4,532,155 A | * | 7/1985 | Golant et al. ................ 427/213 |
| 4,721,747 A | * | 1/1988 | Doshi ................... C09D 201/06 523/511 |
| 5,106,838 A | * | 4/1992 | Reinhart .................. A61K 8/37 514/59 |
| 5,130,171 A | * | 7/1992 | Prud'Homme .......... A01C 1/06 424/462 |
| 5,223,559 A | * | 6/1993 | Arraudeau et al. ............. 524/47 |
| 5,246,780 A | * | 9/1993 | Farer ....................... A61K 8/11 424/63 |
| 5,356,617 A | * | 10/1994 | Schlossman ......... A61K 8/0204 424/401 |
| 5,486,631 A | * | 1/1996 | Mitchnick ............. C07F 7/0859 556/10 |
| 5,554,217 A | * | 9/1996 | Babler ................ C08K 3/0033 106/31.66 |
| 5,763,086 A | * | 6/1998 | Schmid et al. ............... 428/404 |
| 6,720,072 B1 | * | 4/2004 | Hinterwaldner et al. .... 428/403 |
| 2003/0118532 A1 | * | 6/2003 | Taniguchi et al. .............. 424/63 |
| 2004/0265348 A1 | * | 12/2004 | Hollenberg ............... A61K 8/11 424/401 |
| 2005/0260149 A1 | * | 11/2005 | Elliott ..................... A61K 8/29 424/63 |

FOREIGN PATENT DOCUMENTS

| | | | | |
|---|---|---|---|---|
| DE | 4020316 | * | 1/1992 | |
| JP | H0999246 | * | 4/1997 | ............... A61K 8/00 |
| JP | 2001181136 | * | 7/2001 | ............... A61K 8/18 |
| JP | 2004-315378 | | 11/2004 | |
| WO | WO 200022052 | * | 4/2000 | |

OTHER PUBLICATIONS

MCWDN website, Mixture, accessed Feb. 1, 2010, p. 1.*

* cited by examiner

*Primary Examiner* — Tabatha Penny
(74) *Attorney, Agent, or Firm* — Handal & Morofsky, LLC; Anthony H. Handal; Mona Roy

(57) ABSTRACT

A hybrid coating material and process for pigments and other powders, for example cosmetic powders employs an organometallate, for example a titanate, and a functionalized silicon compound, for example a trialkoxysilane or a functionalized polysiloxane, which covalently bond to each other and to the substrate powder. The coated powders can exhibit excellent hydrophobicity coupled with lipophilicity. Employment of fluorinated silicon compounds may provide hydrophobicity and lipophobicity. Examples show good dispersibility of coated pigments in aqueous, oil and silicone fluids.

31 Claims, No Drawings

HYBRID COATED COSMETIC POWDERS AND METHODS OF MAKING AND USING SAME

CROSS-REFERENCE TO RELATED APPLICATIONS

This Application claims the benefit of Scholssman et al. U.S. provisional patent application Ser. No. 60/451,056, filed Feb. 28, 2003, U.S. provisional patent application Ser. No. 60/472,527, filed May 22, 2003, and is a division of U.S. Utility application Ser. No. 10/791,424, filed on Mar. 1, 2004, the disclosures of each of which patent applications are hereby incorporated herein by reference thereto.

STATEMENT REGARDING FEDERALLY SPONSORED RESEARCH OR DEVELOPMENT (Not applicable.)

BACKGROUND OF THE INVENTION

The present invention relates to novel hybrid coated cosmetics powders and methods of making and using same. More particularly, the invention relates to novel compositions and methods for coating insoluble cosmetics powders, for example inorganic and organic, pigments and fillers, to the coated powders produced, to cosmetic and other formulations incorporating such coated powders and to methods of making and using said coated powders and formulations. Preferred embodiments of the invention include novel coated cosmetic powders having a unique combination of excellent hydrophobic and lipophilic properties which is particularly advantageous in many cosmetic applications.

Most cosmetics formulations include in their compositions cosmetic powders, finely divided particles of solid, insoluble materials, for example pigments and fillers, that can serve a variety of functions, such as providing desired visual properties such as opacity and color, desired tactile properties such as viscosity and feel, special effects such as pearlescence and iridescence and various other desirable properties, for example oil absorbency. Cosmetic powders include inorganic materials such as metal oxides, silicates and carbonates as well as organic pigments or lakes such as ultramarine and crimson lake and polymeric particulates such as nylon and cellulose. Additional examples of pigments that can be employed in the present invention are set forth hereinbelow. Some examples of cosmetic formulations employing powders include liquid or powder makeups and foundations, moisturizing and antiaging creams and lotions, nail polish, lipstick, mascara and eye shadow, to name but a few.

Primarily because of their surface characteristics, it may be difficult to satisfactorily incorporate raw, untreated powders into liquid or powdered cosmetic bases or excipients in a manner providing uniform stable dispersions. Desirably, the powders should be uniformly distributed throughout the base or excipient medium and the dispersion should remain stable over time with no significant settling or agglomeration occurring before the product is eventually used by the end consumer, which can be as much as two or more years after manufacture. It is also desirable that the powders should not impart unaesthetic characteristics to the end-product cosmetic formulation, such as a gritty or sandy feel, which may result from agglomeration of powder particles or the presence of oversized particles in the pigment powder, discoloration attributable to non-uniform distribution of the powder, and other negative characteristics such as settling.

Many pigment materials for example metal oxides and carbonates, have a somewhat hydrophilic surface, or bear hydrophilic moieties or ions on their external surfaces which render the powder particles prone to agglomerate in aqueous media which are commonly employed in cosmetics.

Accordingly, over the years, many compositions and methods have been employed and proposed for treating or coating insoluble cosmetic powders, in order to overcome these and other problems. Such prior proposals have met with considerable success and it is now standard practice in the cosmetics industry to coat powders for cosmetic use. In particular, it is well known to "hydrophobize" cosmetic powders, which is to say to treat the powders to render them more hydrophobic, thus providing more stable dispersions (or suspensions) in aqueous media.

Powders can be hydrophobized by treatment with a suitable coating agent in a liquid medium, for example by mixing or spraying the coating agent with or on to the powder and heating the mixture, optionally under vacuum to remove volatile solvents, if employed. Preferred coating agents are chemically reactive with the substrate powder to provide a durable covalent bond thereto and have hydrophobic chemical backbones or substituents that can provide a hydrophobic outer layer, skin or shell around each individual powder particle. The coating agent may react, for example, with hydroxyl groups, oxide ions, available oxygen atoms or other suitable reactive groups normally present on the surface of the cosmetic powder being coated.

Mitchell Schlossman U.S. Pat. No. 4,877,604 ("Schlossman '604" hereinafter), the disclosure of which is herein incorporated by reference thereto, discloses and claims the use of organotitanates, to coat pigments and other cosmetic powders, one preferred coating agent being isopropyl titanium triisostearate. Schlossman '604 discloses that the claimed coating materials and methods can provide uniform and stable dispersions of pigments and other cosmetic materials, such as talc, sericites and mica. Such dispersion uniformity can avoid the need to colloid mill the final emulsion to achieve smoothness and homogeneity in various cosmetic products, for example, in oil-in-water liquid makeups, avoiding settling or segregating out of pigments or other cosmetic material thereby increasing the shelf-life of the product. In addition, the use of Schlossman '604's titanate-treated pigments in liquid pigment and/or color extenders can improve the viscosity range providing more uniform extenders and enabling extenders to be utilized without adversely affecting the viscosity of the final product.

Other advantages to using treated or coated materials in accordance with Schlossman '604 include increased water resistance due to hydrophobic characteristics, reduced need for powder blends, increased smoothness on application of anhydrous and powder blends, better skin adhesion, better appearance of frosted products, less streaking in pressed and anhydrous makeup products and noticeable smoothness and ease of manufacture of compact cream makeup.

Thus, the Schlossman '604 organometallate coating materials provide an array of attractive features. Pursuant to the insights of the invention, it would be desirable to provide coatings for cosmetic powders which retain these benefits and which can extend potential uses of the resultant coated powders to environments where isopropyl titanium triisostearate treated pigment may not always be satisfactory, for example in silicone fluids and in low pH media. The latter are often required for skin care products containing alpha-hydroxy acids.

It is also known to employ functionalized silanes, including for example, triethoxy octylsilane to provide a silicone coating on cosmetic powders to render them hydrophobic. With regard to terminology, it is notable that even extensively substituted derivatives of silane, such as triethoxy decyl silane are sometimes generally referenced in the art by the catch-all phrase "silanes". While silane-coated powders may display good hydrophobicity they may not be adequately lipophilic for some purposes yielding unacceptably viscous dispersions in cosmetic oils such as mineral oil. A further problem is that silicone coated pigments may display color shift over time. Hollenberg et al. U.S. Pat. No. 5,143,722 is but one example of a disclosure of silane coated cosmetic pigments providing silicone coated pigment powders.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the invention.

BRIEF SUMMARY OF THE INVENTION

The present invention solves the above mentioned problems of the related arts by providing a process of coating any one or more of a wide range of cosmetic or other powders with a novel hybrid coating agent comprising reacting a combination of a an organotitanate or other suitable hydrophobizing organometallate and a functionalized silicon compound with the powder or powders to produce hybrid coated powders. The invention enables a wide range of powders to be effectively coated to have a number of desirable properties such as good water repellency, good stability, a smooth feel and good adhesion to the skin to be produced. The powders that may be coated include common cosmetic powders such as metal oxide pigments and metal carbonate, silicate or other fillers, as well as more exotic powders such as sericites and metal oxide coated micas. Preferred hybrid coated powders of the invention display all of these properties. The invention also provides novel processes for producing the coated cosmetic powder and cosmetics made with the treated pigment or other powder.

Preferably, both the organometallate and the functionalized silicon compound are sufficiently reactive to covalently bond with the powder and each have chemical structures providing hydrophobicity to the coated powder. In addition it is particularly preferred that organometallate and the functionalized silicon compound are capable of reacting with each other. Preferably also, the organometallate and silicon compound are selected so as to avoid impeding each other's functionality.

The functionalized silicon compound can be any one, or a mixture, of a wide range of compounds including a functionalized silane, a functionalized silicone, e.g. a polysiloxane, or fluorinated analogs of the foregoing.

In one embodiment, the invention provides a cosmetic powder, for example a pigment, extender pigment or filler, treated or coated with a hybrid coating agent comprising an organic titanate and a trialkoxyalkylsilane. After reaction in the processes of the invention, for example by heat treatment, these compounds become chemically bonded to the surface of the pigments or fillers.

Coated pigment powders according to the invention may have both hydrophobic and lipophilic properties or both hydrophobic and lipophobic properties. Use of fluorinated silicon compounds can provide the lipophobic properties.

Some embodiments of coated pigment powder according to the invention have hydrophobic and lipophilic properties and are also dispersible in silicone fluids.

The treated pigments have good adhesion to the skin, and ability to permit color pigment of fine particle size to spread well, and is particularly suitable for use in cosmetics such as powder, oil-in-water and water-in-oil emulsions and anhydrous makeup like lipstick.

DETAILED DESCRIPTION OF THE INVENTION

The present invention provides a process for hydrophobizing a variety of cosmetic powders, including pigments, lakes of organic colorant and filler, and formulations in which the such treated powders can be applied. The invention extends to the coated powders produced, to the novel methods of formulating cosmetic products and to the novel cosmetic products that result. In particular, the invention provides novel coated powders, especially but not exclusively cosmetic powders, which, in preferred embodiments of the invention, are highly hydrophobic and uniquely dispersible in both hydrocarbon-based oils, or lipids, and in silicone fluids.

These desirable properties can be obtained by coating any one or more of a wide range of cosmetic powders with a novel combination of coating agents pursuant to the invention, namely an organometallate and a reactive silicon compound, to provide a durable hybrid coating on the powder particles.

It is desirable that both coating agents are sufficiently reactive to covalently bond with the target particles, under the conditions of the coating process, to provide a reaction product which is stable to subsequent processing and storage conditions.

It is preferred that each coating agent residue becomes chemically covalently bound to the surfaces of the powder particles and contributes to the provision of a durable outer layer or skin of a hybrid chemical nature, including metal atoms, silicon atoms and possibly M-O—Si groups, as described herein, which layer or skin envelops each powder particle.

Preferably at least one of the coating agents comprises a bifunctional coupling agent capable of covalently bonding not only with the target substrate powder but also with the other coating agent or one of the other coating agents if more than two are employed. To this end, the bifunctional coupling agent may have two or more functional entities, which may be the same or different and which between them provide the desired reactivity with the substrate powder and the other coating agent or materials. More preferably, both coating agents are bifunctional, providing the possibility of oligomeric or polymeric chains comprising residues of both starting materials being present in the coating.

The beneficial high dispersibility in two different classes of liquid media, coupled with excellent hydrophobicity and water repellency, is especially attractive to formulators in the cosmetics industry enabling the inventive hybrid coated powders to be specified for a wide range of applications without undue concern as to the nature of the liquid phase into which the powder is to be dispersed. Furthermore, the inventive hybrid coatings are suitable for a wide range of cosmetic powders including many or most of the powders used in everyday cosmetic products such as liquid or powder makeups, lipsticks, nail enamels, eye shadows, mascaras and so on. Thus the formulator may freely specify cosmetic powders having the inventive hybrid coatings to meet an exceptionally diversified range of cosmetics requirements. The invention further more enables the formulator to specify one type of coating, the hybrid coating of the invention to be employed for all the powder ingredients of a cosmetic formulation without concern as to the liquid media to be employed in the formulation or as to possible incompatibilities between different coatings.

Possibly, one of the coating agents, for example the organometallate, may comprise a bifunctional coupling agent, as described above, while the other coating agent, in this exemplary case the silicon-containing compound, is reactive with the one coating agent but not the target powder, for example by way of a hydroxyl substituent. Such a combination can provide a bilayer shell-like coating on the particles comprising for example an outer shell of silicon-containing moieties, being the residues of the silicon-containing compound coupled to the substrate powder through an inner shell of organometallate residues.

In one preferred embodiment, the invention relates to cosmetic powders treated with a mixture of organotitanate and trialkoxy alkylsilane coating agents to provide a coating that is hydrophobic and lipophilic or lipophobic. The invention also provides processes for the production of such coated powders and cosmetic formulations comprising the cosmetic powders treated with the novel combination of coating compounds or agents.

Organometallates

Any organometallate compatible with the purposes of the invention may be employed in the novel compositions, materials and processes described herein. Many suitable organometallates, and equivalent compounds, additional to those described or suggested herein will be apparent to those skilled in the art in light of the disclosure herein or will become apparent as the art develops. Non-limiting examples of equivalent compounds or compositions are compounds or compositions which function as precursors yielding one or more suitable organometallates in situ.

Organometallate compounds to be employed in the invention are preferably chosen to provide hydrophobic residual units in the powder coating. They may, for example, comprise metallate compounds wherein at least one enduring, unreactive, hydrophobic organic group, such as a saturated hydrocarbon, possibly containing one or more phenyl groups, is each attached to a metal atom by an oxygen atom and at least one displaceable groups or atoms is also attached to the metal atom by an oxygen atom to provide a functional group. The enduring group endures to become a hydrophobic residue in the powder coating while the functional group is removed in the coating process, preferably yielding an M-O group in the coating compound. The residue in the coating should be cosmetically compatible. For this reason, organometallates of toxic metals such as lead, cadmium and mercury are to be avoided.

To this end the organometallate compounds may comprise one or more relatively unreactive hydrophobic organic groups, e.g. ester groups, covalently bonded to a metal atom, and one or more relatively reactive groups, or functional entities e.g ether or alkoxy groups, also covalently bound to the same metal atom.

The organometallate compound can have from one to five functional entities depending upon the valence state of the metal. However from one to three functional entities is preferred with organometallic compounds having two functional entities for example two alkoxy groups, especially two methoxy or two ethoxy groups, being particularly preferred for use in the practice of the invention. Organometallates with two or more functional entities may be described as "coupling agents".

Some suitable organometallate compounds for use in the present invention have a structure illustrated by the following Formula 1

$$(R^1O—)_xM(—OOCR^2)_y \qquad (1)$$

wherein:
$R^1$ is a saturated, unsaturated or polyunsaturated, straight chain, branched or unsubstituted or substituted cyclic alkyl group having from 1 to 12 carbon atoms, preferably from 1 to 4 carbon atoms;
$R^2$ is a saturated, unsaturated or polyunsaturated, straight chain, branched, unsubstituted cyclic, substituted cyclic alkyl or alkyl phenyl group having from 3 to 60 carbon atoms, preferably from 7 to 25 carbon atoms;
M is a cosmetically compatible metal capable of forming the compound shown with a valence state of z; and $x+y=z.$ In some useful or preferred embodiments of the invention:
$R^1$ is a saturated straight chain or branched alkyl group having from 1 to 4 carbon atoms, for example, methyl, ethyl or isopropyl;
$R^2$ is a saturated straight chain or branched alkyl group having from 7 to 25 carbon atoms, for example octyl, decyl, stearoyl, or cumyl; and
M is a metal with a valence state, z, of 2, for example zinc, a metal with a valence state, z, of 3, for example aluminum, a metal with a valence state, z, of 4, for example, tin, titanium or zirconium, or a metal with a valence state, z, of 5, for example vanadium. Metals with a valence state of 3 or higher are preferred.

In the following description, where reference is made to titanium or to organotitanate compounds it will be understood that other metals or organometallates such as tin, vanadium, zinc and zirconium and their organometallates that are suitable for the purposes of the invention may be used mutatis mutandis in place of titanium or organotitanates, unless the context suggests indicates otherwise.

The organotitanate structures illustrated by Formula 1 and which can be employed in the practice of the invention include, for the case where M is titanium, not only mono-alkoxy titanates, but also di- and tri-alkoxy titanates. Monofunctional organometallates, such as monoalkoxy titanates, can couple to the pigment surface and also to suitably functionalized silicones. However, multifunctional organometallates, for example di- and tri-alkoxy titanates, are particularly advantageous for use in the invention for and can provide a number of benefits such as: greater reactivity of the organometallate, for example enhanced ability to bind to the substrate powder; ability to catalyze reaction of functionalized silicon compounds with substrate the substrate powder and with the titanate; and the ability to crosslink with reactive silicon compounds.

Some limited polymerization of multifunctional organometallates may occur with bonding of the resultant oligomers or polymers to the powder substrate. However, it is believed that such organometallate oligomers or polymers in many cases may not be sufficiently stable to yield residues in the end-product coated powders or may not survive post-processing, for example formulation into creams or lotions.

Some suitable hydrophobizing organometallate compounds for use in the practice of the present invention include organotitanate compounds of the following Formula 2:

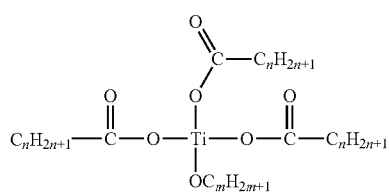

(2)

wherein:
m is from 1 to 4; and
n is from 7 to 25, preferably from 12 to 20.

The length of each fatty acid chain may be the same or different.

It will be understood that other suitable organometallate compounds can be employed wherein in Formula (2) titanium is replaced by a suitable metal such as aluminum, tin, vanadium, zinc or zirconium with the formula being adjusted for the metal valence state, as may be necessary, for example by adjusting the number of ester groups, the alkoxy group being retained. Thus, suitable organoaluminates, organostannates, organovanadates, organozincates or organozirconates may be employed Some specific organometallates suitable for use in the invention include: liquid monoalkoxy ($C_1$ to $C_{20}$) isostearoyl titanates, especially isopropyl triisostearoyl titanate; isopropyl dimethacryl isostearoyl titanate and isopropyl dimethacryl isostearoyl titanate and coordinate titanates such as tetraisopropyl (di(dioctyl) phosphito titanate and tetra (2,2 diallyoxymethyl) butyl, di(ditridecyl) phosphito titanate; organotitanates disclosed in "*The Chemistry of Titanate Coupling Agents*", pages 2-9 and 26-29 in "Ken-React Reference Manual—Titanate, Zirconate and Aluminate Coupling Agents", Monte et al., M. Schlossman U.S. Pat. No. 4,877,604; and the titanate coupling agents disclosed in Monte et al. U.S. Pat. No. 4,098,758, the disclosure of each of which references is hereby incorporated herein by reference thereto.

Other organometallates that may be used include:
isopropyl tri(dioctyl)pyrophosphato titanate, di(dioctyl) pyrophosphato oxoethylene titanate, di(dioctyl) phosphato ethylene titanate, di(dioctyl)pyrophosphato ethylene titanate, tetraoctyl titanate di(ditridecyl) phosphite, and dialkoxy bis(triethanolamine) titanate;
aluminates such as diisopropyl acetoalkoxy aluminate, isopropyl diisostearoyl aluminate, and isopropyl dioctyl phosphato aluminate;
zirconates such as isopropyl triisostearoyl zirconate, butyl triisostearoyl zirconate, butyl trioleoyl zirconate, isopropyl trilinoleoyl zirconate, di(cumyl)phenyl oxoethylene zirconate, di(cumyl)phenyl dibutyl zirconate and tri(cumyl)phenyl propyl zirconate; and
vanadate and zincate analogs or equivalents of the foregoing.

Other coupling agents can also be used with similar effect and advantage, for example, zirconate or aluminate coupling agents such as neopentyl (diallyl) oxyl, tri(dioctyl) phosphito zirconate and equivalent aluminates. However, titanates constitute a preferred species. Furthermore, analogous titanate coupling agents having different proportions of hydrolyzable to non-hydrolyzable groups from those disclosed by Monte, can be used. There is a great diversity of substituents that can be present on the coupling agent. Some examples of these are set forth in Monte (supra). Others will be apparent to those skilled in the art in light of the disclosures herein. Still others may become apparent as the art develops.

Still further organometallates providing cosmetically compatible residues that can be employed in the present invention will be known to the art. Some of these further organometallates are disclosed in: Guillissen U.S. Pat. No. 2,732,320, for example at column 4, lines 25-42; Kohn et al. U.S. Pat. No. 3,014,826, for example at column 2, lines 17-23; Rauner U.S. Pat. No. 3,015,637, for example at column 2, line 39 to column 3, line 3; Hartlein U.S. Pat. No. 3,647,846 (Dow Corning) for example at column 2, lines 34 to 63; Ona et al. U.S. Pat. No. 4,399,247 for example at column 4, line 35 to column 5, line 18; the disclosures of which patents are hereby incorporated herein by reference thereto.

If desired, the organometallate may be chelated, for example by a mono- or polydentate chelating ligand or group which can be bonded to the organometallate such, for example, as one or more ethylenically unsaturated groups (e.g. acrylic, methacrylic or vinylic), halogenated groups, hydroxylated groups, carboxylated groups, thiol groups, epoxy groups, ester groups, amine groups, urea groups, urethane groups, acetoacetate groups or a group derived from EDTA and its derivatives. Some examples of possible chelating groups or ligands include carboxylic acids, □-ketones, □-diketones, □-keto esters, □-keto amines, (□- and □-hydroxy acids, amino acids, preferably □-hydroxylated amino acids, salicylic acid and derivatives thereof, some specific examples of which are acetoacetoxyethyl methacrylate, methyl □-hydroxymethacrylate, —N-methacryloyl-L-lysine, 4- or 5-methacrylaminosalicylic acid.

While the invention is limited not by any particular theory, but only by the accompanying claims, it is contemplated that the organometallate compound will catalyze, promote or participate in the binding of the functionalized silicone compound with the substrate powder particles. Such favorable activity is helpful in assuring more complete reaction of the functionalized silicone compound, leading to stable coatings with low proportions of unreacted functional entities. Such higher stability is believed to be of particular value for the coating of pigments in preventing or eliminating color shift over time, a problem which may occur with conventionally coated pigments. Such control of color shift is of particular value in the cosmetics and other industries where high quality and consistent appearances are demanded by end product consumers.

Functionalized Silicone Compounds

Any suitably functionalized silane, functionalized polysiloxane, functionalized fluorinated or fluoroalkyl silane or polysiloxane, or other appropriate functionalized silicon compound compatible with the purposes of the invention, may be employed as a coating agent in the novel compositions, materials and processes described herein. Preferably, the functionalized silicone compound employed is provided with at least one functional entity capable of covalently bonding to a target pigment surface, either directly or through an organometallate residue, under the reaction conditions employed in the coating processes of the invention.

A preferred functional entity is a lower alkoxy group covalently bonded directly to a silicon atom and having from one to four carbon atoms. Other functional entities such as halo atoms, preferably chloro, amino groups, imino groups, and/or hydroxyl groups may be employed, as is known to those skilled in the art. Still other functional entities or groups that may be employed if desired, so long as they provide adequate coupling functionality for the purposes of the invention include ethylenically unsaturated groups such as acrylic, methacrylic, vinylic groups or the like, halogenated groups, hydroxylated groups, carboxyl or carboxylated groups, thiol or mercaptan groups, epoxy groups, ester groups, urethane groups, urea groups, amino acid groups, polypeptide groups and so on.

Furthermore, groups that are largely unreactive in conventional coating processes, for example Si—H groups in polysiloxane compounds, e.g. methicone, may have sufficient reactivity in the presence of the organometallate compounds employed in the present invention to be useful as functional entities. Thus, for example, methicone, having a backbone of methyl hydrogen sioxy groups can be employed as a functionalized silicone compound in the practice of the invention without addition of other functional entities. Equivalent compounds having fewer reactive backbone hydrogen atoms may also be employed.

It can also be advantageous for the silicone compound to have multiple functional entities, for example methoxy or ethoxy groups, to enable the functionalized silicone compound to become polymerizes, and possibly even cross-linked, as a result of the coating processes of the invention.

The functionalized silicon compound employed in the coating process of the invention should preferably have a structure which will provide a stable residue on the substrate powder and which will remain stable throughout subsequent processing steps, for example cosmetic formulation steps, that the coated powder is intended to undergo, and will also remain stable for the intended shelf life of the product. The silicon backbone structure of the functionalized silicon compound starting material, and the substituents employed, should be selected with this end in view. Thus, it is preferred that the backbone structure comprise a single silicon atom, a pair of silicon atoms connected by a single covalent bond or a siloxy chain, —(—Si—O—)$_r$, where r may be an integer of from 2 to 200, or even as high as 1,000. Preferably r is from 5 to 100, more preferably from 10 to 50.

Preferred substituents in the silicon compound, besides the functional entity or groups, lack chemical reactivity in the processes of the invention and form stable entities in the powder coating. Some examples of suitable such nonfunctional substituents include saturated hydrocarbon groups and saturated fluorohydrocarbon groups, particularly, but not exclusively, alkyl and fluoroalkyl groups. Such substituents can have any number of carbon atoms supporting stable bonding of the substituent or substituents to the silicon backbone, for example, from 1 to about 50, preferably from 4 to about 35 and more preferably from about 7 to about 25 carbon atoms per substituent, preferably with a maximum of 50 carbon atoms per silicon atom. It will be understood that increasing the carbon count of the substituent or substituents may enhance the lipophilicity of the inventive coated powders. However, this consideration will need to be balanced against the instability of larger substituents which may dissociate. Another balancing consideration is that for enhanced silicone dispersibility, higher proportions of silicon atoms in the coating may be desirable.

Many suitable functionalized silicon compounds, and equivalent compounds, additional to those described or suggested herein will be apparent to those skilled in the art in light of the disclosure herein or will become apparent as the art develops.

Some suitable functionalized silane compounds for use in the present invention have a structure illustrated by the following Formula 3:

wherein:
R$^3$ is methyl, ethyl propyl or butyl;
R$^4$ is a saturated, unsaturated or polyunsaturated, straight chain, branched, unsubstituted cyclic, substituted cyclic alkyl or alkyl phenyl group having from 3 to 60 carbon atoms, preferably a saturated alky group having from 7 to 25 carbon atoms; and x+y=4.

The structures depicted include mono- and dialkoxy silanes in addition to trialkoxysilanes, all of which can react with pigment surfaces, However, di- and tri-alkoxy silanes are particularly advantageous for their abilities to form polymers (or oligomers) and crosslinked networks which are chemically and physically stable. In practice, trialkoxysilanes, such as those specifically mentioned herein are particularly suitable for employment in the invention being active and commonly used as functionalized silicon coating materials.

Some preferred functionalized silicon compounds for use in the practice of the invention have the following Formula 4:

wherein R$^3$ and n are the same as above and preferably R$^3$ is methyl or ethyl and n is from 7 to 25.

Some examples of suitable functionalized silanes include: organoalkoxysilanes having an organic group or groups which may be unsubstituted or substituted or a mixture of different groups including for example, methyltrimethoxyalkylsilane, phenyltrimethoxyalkylsilane, and diphenyldimethoxy alkylsilane, as well as silanes having aryl-substituted organic groups, for example, gamma-methacryloxypropyl-trimethoxysilane wherein the alkyl group preferably has from 7 to 25 carbon atoms, more preferably from 8 to 12 carbon atoms and the aryl group is preferably a saturated hydrocarbon, save for benzene ring unsaturation, for example phenyl or alkylphenyl with up to 25 carbon atoms.

Functionalized silicon compound coating agents, or starting materials, employable in the invention can include suitable polysiloxanes such for example as a polysiloxane compound of the following Formula 5:

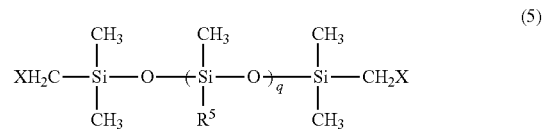

wherein:
R5 is CH3 or H;
X is H or OH; and q is from 1 to about 1,000, preferably not more than about 100 and more preferably from about 5 to about 60.

The $R^5$ substituents can all be hydrogen or all be methyl with the presence of hydrogen rather than methyl being desirable for higher values of q to provide additional reactive sites. Alternatively, the $R^5$ substituents can be a mixture of hydrogen and methyl groups, for example a 1:1 mixture. The mixture can be any desired proportion of the two substituents, for example from 3:1 to 1:3. "Mixture" is here used to indicate that one or more siloxy units has a hydrogen substituent at $R^5$, and one or more siloxy units has a methyl substituent at $R^5$.

This structure includes three classes of polysiloxane compound that are commonly used to coat pigments especially cosmetic pigments, namely: methyl hydrogen polysiloxane wherein X=H and R=$CH_3$; methyl hydrogen polysiloxane and dimethylpolysiloxane copolymer wherein X=H, R=$CH_3$ or H; and dimethiconol wherein X=OH, R=$CH_3$. Compounds containing methyl hydrogen polysiloxane can bond chemically to the powder substrate by reaction of a Si—H group while dimethiconol can bond to the pigment or other powder, chemically via crosslinking through reaction with a di- or tri-alkoxy titanate. Suitably functionalized dimethicone compounds may also be employed, with either backbone or terminal functional substituents. Useful functionalized polysiloxanes can comprise from about 1 to about 100 siloxy groups per functional group, desirably from about 3 to about 20 siloxy groups per functional group.

The polysiloxane compounds, groups or units employed in the invention or generated in the coating may include polymeric chains having up to 100 or even up to 1,000 repeating —Si—O— units, wherein at least one Si atom of each chain is linked to the powder surface through an oxygen atom. The chains can be cross-linked to each other as well. The remaining functional sites of each Si atom in the chain can be occupied by a variety of groups as will be apparent from this disclosure, including hydrogen, methyl, $C_2$-$C_{30}$ alkyl or alkenyl, and/or phenyl, and equivalents thereof, resulting in units such as —Si($CH_3$)($C_6H_5$)O—, —Si($CH_3$)(H)O—, or —Si(H)($C_6H_5$)O—, and generally capped with —Si($CH_3$)$_3$.

Some further examples of embodiments of functionalized silicones useful in the practice of the invention include alkoxy-substituted branched silicones of intermediate size, having for example from about 10 to about 100 siloxy groups per molecule, preferably from about 15 to about 40 siloxy groups per molecule. Optionally, such a branched silicone can have a relatively long backbone of for, example from about 4 to about 50 siloxy units, preferably from about 8 to about 30 siloxy units, with a small number of side chains, for example from about 1 to about 10 side chains, preferably from 2 to 5 side chains. The side chains can have the same or different numbers of siloxy groups, for example from about 1 to about 12 siloxy groups, preferably from 3 to 8 siloxy groups.

Such a branched silicone can be functionalized with a small number of alkoxy groups, e.g. methoxy or ethoxy groups, preferably methoxy groups, for example from about 1 to about 10 alkoxy groups, preferably from 2 to 5 alkoxy groups. Preferably, the alkoxy groups are not terminal groups, although some could be, and preferably they are attached to the backbone of the branched silicone. However, in other embodiments one or more alkoxy groups can be attached to one or more side chains, if desired.

In still further embodiments of such branched silicones one or more, or all, of the alkoxy groups can be replaced by another suitable functional group as described herein, for example a chloro group.

The siloxy groups are preferably dimethylsiloxy groups, or possibly diethylsiloxy groups although other lower alkyl groups, e.g. up to about 10 carbon atoms may be attached to the silicone atoms, if desired, as will be apparent to those skilled in the art. A small number, e.g. less than 10, of the siloxy groups may be methyl hydrogen siloxy groups if desired. If methyl hydrogen siloxy groups are employed fewer or no alkoxy or other functional substituent may be required.

One specific example of a suitable such branched silicone compound is product KF-9908 supplied by Shin-Etsu Chemical Co., Ltd. (Tokyo, JP) which is believed to have the following formula (6)

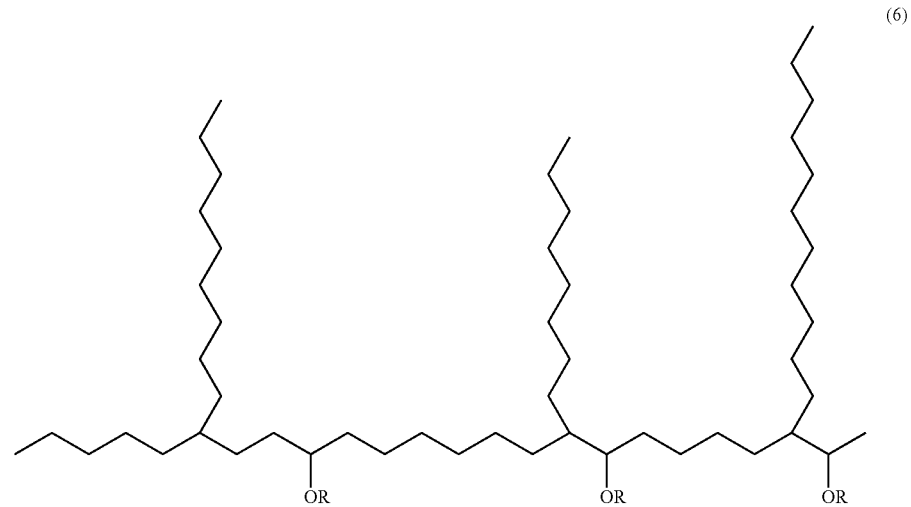

(6)

wherein each node or angle represents an oxygen or silicon atom and the siloxy chains are methyl-terminated dimethyl siloxy chains. The —OR groups are methoxy or ethoxy.

Some alternative embodiments of branched silicone compound useful in the practice of the invention are similar to those just described with the addition of a number of alkyl side chains attached to the siloxy backbone, of length of from about 1 to about 30 carbon atoms. Optionally the alkyl side chains can be interposed between the siloxy side chains to alternate with the siloxy side chains. An example of such a compound is product KF-9909 available from Shin-Etsu Chemical Co.

A still further alternative group of compounds constituting functionalized silicone compounds useful in the practice of the invention comprise compounds complying with formula (6) as described above, wherein the backbone or main chain is a polyacylate chain rather than a polysiloxy chain, the side chains being siloxy chains, as described above, rather than alkyl groups. The acyl monomers of the polyacylate backbone can have from about 1 to about 10 carbon atoms, preferably from 2 to 5 carbon atoms.

Employment of polyfunctional silicon starting materials having more than two functional entities per unit can provide a crosslinked coating of exceptional durability.

Many suitable functionalized silicone compound starting materials, comprising one or more functionalized silicone compounds, that are useful in the practice of the invention are known and some are described, by way of example in: Law, et al. U.S. Pat. No. 4,113,665 (Ameron), for example at column 2, lines 13 to 47 and column 3, line 17 to column 7, line 19; Socci, et al. U.S. Pat. No. 4,832,944 (Revlon), for example, at column 2, lines 21-51; Hollenberg, et al. U.S. Pat. No. 5,143,722, for example at column 2, line 43 to column 3, line 62; Hasegawa U.S. Pat. Nos. 5,368,639 and 5,458,681 (Miyoshi Kasei), for example at column 2, line 24 to column 2, line 48 of the '639 patent; Mitchnick, et al. U.S. Pat. No. 5,486,631 (Siltech and SunSmart), for example at column 2, line 49 to column 4, line 38; Mitchnick, et al U.S. Pat. No. 5,536,492 (Siltech and SunSmart); Horino, et al. U.S. Pat. No. 6,200,580 (Miyoshi Kasei) for example at column 3, lines 33-53 and column 6, line 55 to column 7, line 67; and Colton, et al. United States Patent Application 20020061407 (PPG) for example at paragraphs [0020]-[0022]. The specific passages cited, as well as the entire disclosures, of each of the patent publications identified in this paragraph are hereby incorporated herein by this specific reference thereto.

Some other suitable functionalized silicone compound starting materials useful in the practice of the invention include fluorinated or alkyl fluorinated analogs of the silicone compounds described in the foregoing patents, which fluorinated or alkyl fluorinated analogs can, without this being a requirement, have the desirable structural characteristics for fluorinated or alkyl fluorinated functionalized silicone compound starting materials to be employed in the present invention that are described hereinbelow.

The invention also includes the modification of known silicone coating processes and products such as those described in the foregoing patents or other literature, by the inclusion of an organometallate in the described silicone coatings or processes to provide hybrid silicone-organometallate coated powders. Furthermore, the present invention can include in its processes and products the use of reagents, reactants, reaction conditions and treatment methods and steps described in the foregoing patents or other literature for the purpose of coating powders with silicon-containing materials, as will be understood by those skilled in the art in light of the teachings herein.

Fluoro- and Fluoroalkyl Silicon Compounds

If desired, the functionalized silicon compound starting material may be fluorinated and thereby provide fluoro substituents in the powder coating. Fluorinated silicon compounds have excellent hydrophobicity but relatively poor affinity for lipids, are expensive and may be unstable at an alkaline pH.

Such fluorination, or perfluorination wherein a carbon atom is fully fluorinated, may comprise one, two, three or more fluoro substituents each in one or more hydrocarbon groups, being groups attached directly to a silicon atom in the silicon compound. If saturated, which is preferred in the practice of the invention, such fluorohydrocarbon groups may be expected to manifest themselves in the coating agent in a chemically unchanged state. In one embodiment, the functionalized silicon compound comprises a single fluoroalkyl group having not more than about 30 carbon atoms and from 1 to about 12 fluorine atoms.

Alternatively, the fluorination of the silicon compound could comprise one or two fluorine atoms bonded directly to a silicon atom. However, Si—F groups are less preferred because the resultant residue in the coating may have undesirable reactivity.

Some embodiments of the invention can employ as starting materials one or more fluorosilane compounds having the structure shown in the following Formula 7:

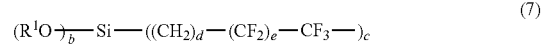

(7)

wherein:
R$^1$ is as defined above, broadly stated, a 1-12 carbon hydrocarbon;
b is 1, 2 or 3;
b+c=4;
d is from 0 to about 3; and
e is from about 3 to about 20.

It will be understood that other functional groups than the alkoxy groups can be employed if desired and that the fluoroalkyl group shown may be used in other compounds where a fluoroalkyl group, has been referenced or would be seen to be suitable herein.

In addition suitable fluorinated functionalized silicone compounds that can be used in the practice of the invention are disclosed in: Farer U.S. Pat. No. 6,471,950, for example at column 2, lines 30-63; Goodwin U.S. Pat. No. 5,328,768 (PPG), for example at column 2, lines 6-25; and O'Lenick Jr. et al. U.S. Pat. No. 6,524,705 (Phoenix Research) for example at column 2, lines 38-63 and column 4, lines 37-48.

In addition, fluorinated silicon compounds or fluorosilanes such as those disclosed in U.S. Pat. No. 5,473,038 O'Lenick, Jr. (Siltech) and Arnaud U.S. Pat. No. 6,203,780 (L'Oreal) can be employed as starting materials for the coating processes of the present invention when suitably functionalized by the inclusion in the molecule, if not already present, of one or more functional groups, for example hydroxy, methoxy or ethoxy groups, as has been described herein with reference to non-fluorinated compounds. Two or three such groups are preferred to provide for the possibility of a polymerized residue in the coating.

The entire disclosures of each of the foregoing patent publications relating to fluorinated silicon compounds are hereby incorporated herein by this specific reference thereto.

It will be understood that the above-described fluorinated functionalized silicon compounds can be employed in the processes of the invention in place of or as well as the nonfluorinated functionalized silicon compounds to yield coatings including fluorinated groups. If desired, the fluorinated functionalized silicon compounds admixed with, or otherwise combined with the nonfluorinated functionalized silicon compounds, as coating agents, in approximate proportions of from 1:10 to 10:1.

Hydrocarbon Substituents

It will be understood that possible hydrocarbon groups in the organometallate or functionalized silicon compound can have a variety of structures and may, for example, include, independently of each other, if the molecule contains more than one hydrocarbon group, a linear or branched alkyl group, a cycloalkyl group, a substituted or an unsubstituted aryl group or combinations of the foregoing. Preferably, such groups are selected to provide residues having little or more preferably no significant reactivity in the end product coated powder.

If desired, either or both the organometallate or the silicon compound can contain one or more functional coupling groups, or atoms intended to provide a bond to the substrate powder or to the other of the organometallate or the silicon compound, which functional entity is borne by a hydrocarbon or fluorohydrocarbon substituent, for example an alkyl or fluoroalkyl group. Such an alkyl substituent functional group may for example be an ethylenically unsaturated group such as an acrylic, methacrylic, vinylic group or the like, a halogen or halogenated group, a hydroxyl or hydroxylated group, a carboxyl or carboxylated group, a thiol or mercaptan group, an epoxy group, an ester group, a urethane group, a urea group, an amine or amino acid group, a polypeptide group or the like. Where the carrier group for the functional entity is a fluoroalkyl or other fluorohydrocarbon group, it is preferred that there is at least one carbon atom, more preferably at least two carbon atoms between the carbon atom bearing the functional entity and the closest carbon atom bearing a fluorine atom.

However, in most cases, for the purposes of the invention it is believed preferable for the functional entity to be bonded directly to a, or the, metal atom of the organometallate or to a silicon atom of the silicon compound, or at least to be not unduly remote from same. Accordingly, where a functional entity intended for coupling in the coating process of the invention is borne by a hydrocarbon substituent, it is preferred that the functional entity be attached to the fifth or fewer carbon atoms from the metal atom, preferably to an adjacent or next adjacent carbon atom.

Solvents

Suitable solvents for the coating agents may be employed to facilitate the coating process, if desired. Such solvents should be capable of dissolving the respective coating agent to promote even distribution of the coating agent over the surface of the substrate powders in a mixing step and of being removed in a drying step. For example, water or other suitable solvent may be employed for the organotitanate or other organometallate, as described in Schlossman '604 and a suitable aprotic solvent can be employed for the functionalized silane or other silicon compound. Also, if desired, the organometallate, and optionally also the silane, can be solubilized in a volatile organic solvent such as isopropyl alcohol, heptane, isoheptane, isooctane, isononane and petroleum distillates such as those available from Phillips Chemical under the trade names or trademarks Soltrol 130, Soltrol 150 and Soltrol 170. and then mix it with or spray it on the materials to be coated.

Another useful solvent for functionalized silicon compounds is an ISOPAR isoparaffinic fluid. ISOPAR isoparaffinic fluids are a range of solvents each comprising a high-purity, fractionated partially neutralized mixture of isoparaffinic acids which are available in different grades such as ISOPAR C, which comprises C7-C8 solvents, ISOPAR E or ISOPAR G isoparaffinic fluids.

Preferably, a single solvent, for example ISOPAR C isoparaffinic fluid, or a mixture of solvents, is used to dissolve both the organometallate and the functionalized silicon compound in a single homogenous liquid medium. However, an emulsion of two or more solvents could be employed, with different coating agents dissolved in each solvent, on a one-to-one basis.

Cosmetic Powders

Some suitable cosmetic or other powders that can be employed in this invention include: inorganic and organic pigments and fillers; talc; mica; sericite; kaolin; starches; barium sulfate; calcium carbonate; porous or non-porous silica in various shapes including spherical, ellipsoidal, irregular, rod and other known shapes; hydroxyapatite; and hollow or solid polymeric powders or microspheres of polymethylmethacrylate, polyvinylidene chloride copolymer, polyethylene, cellulose or nylon or other suitable polymer. Other suitable cosmetic or other powders will be known or be or become apparent to those skilled in the art.

The powders employed as substrates in the processes of the invention may have any desired regular or irregular shape including spherical or ball like particles with irregular porous surfaces, needles, rods, flakes, rhomboids and so on.

Some suitable inorganic pigments which may benefit from the hybrid coatings of the present invention include: titanium dioxide; zinc oxide; iron oxide; alumina oxide; chromium oxide; mango violet; ultramarines, composites of metal oxides or of a metal oxide and an inorganic salt and any other inorganic pigment powder useful in the cosmetic or other relevant arts. If desired, prior to the inventive coating treatment, powders such as titanium dioxide, zinc oxide and other inorganic pigments or fillers, may be treated with silica, alumina, boron nitride or other known inorganic coatings, singly or in combinations.

Some suitable organic pigments include aluminum, barium, calcium and zirconium lakes of FD&C and D&C grades of Red No. 6, Red No. 7, Red 21, Red No. 27 and Yellow No. 5. Other suitable inorganic or organic pigments will be known or be or become apparent to those skilled in the art.

Preferably, the reactants and reaction conditions employed in the coating processes of the invention are selected to provide covalent bonding to metal oxide, hydroxide, carbonate, silicate or other reactive moieties on the surfaces of the cosmetic powder particles. However, ionic, hydrogen or van der Waals bonding in addition to, or in the alternative, may also provide satisfactory bonding between the coating and the substrate powder particle.

Particle Size

There is no particular limitation as to the particle size of the powders employed in the invention. However, a mean particle size in the range of from about 0.01 to about 100 micron is preferred and a mean particle size in the range of from about 0.01 to about 20 micron is more preferred. Desirably, at least about 90 percent, preferably at least about 98 percent, and more preferably at least about 99.5 percent of the particles lie within the preferred average particle size range. Some preferred powders for use in the invention are free of oversize particles that may impart grittiness and are also free of overly fine particles whose presence may be undesirable in the processes of the invention described herein.

Proportions

The quantity, or proportion of hybrid coating material employed in the present invention can be varied according to the nature of the substrate and can be selected to provide a coated pigment or other cosmetic powder having good water repellency, smooth feel and good adhesion to the skin. To this end, the quantity of coating agent should generally be at least 0.1 percent of the coated product. If the amount is over about 30 percent by weight, the coated powder may be too wet and may tend to agglomerate unacceptably. Thus, in one embodiment the quantity is in a range of from about 0.1 to about 30 percent by weight based on the weight of the coated powder, preferably from about 1 to about 10 percent and more preferably from about 2 to about 5 percent of the weight of the coated powder.

The relative proportion, or ratio, of organometallate to silane can be varied according to the balance of properties desired. Thus, the hydrophilicity may be increased by increasing the proportion of organometallate relative to the silane and the silicone fluid dispersibility can be increased by increasing the proportion of silane relative to the organometallate. Thus, the ratio of organotitanate or other organometallate to silane can be in a range of about 0.1:1 to 10:1, but is preferably in a range of about 0.4:1 to about 3:1. A proportion within about ten or twenty percent of equality is useful to provide a balance of properties.

Coating Process

In one embodiment of a process aspect of the invention, the invention provides a cosmetic powder hydrophobizing process comprising:
 a) combining:
  i) a powder to be coated;
  ii) a liquid dispersion medium sufficient for a slurry;
  iii) an organometallate compound of formula (1); and
  iv) a functionalized silicon compound;
 to form a slurry;
 b) thoroughly mixing the slurry;
 c) filtering the slurry; and
 d) heating the resultant paste to a temperature and for a time effective to yield a dry powder.

Some examples of suitable elevated temperatures are in the range of from about 60 to about 130° C., and of suitable times in the range of from about two to about ten hours. Other suitable times and temperatures will be known to those of ordinary skill in the art, having regard to the materials employed, or can be determined without undue experimentation. Optionally drying may be conducted under vacuum.

The slurry may be prepared in a variety of ways, as will be apparent to those of ordinary skill in the art. For example, a blend of the organometallate and the functionalized silicon compound coating agents can be added to the powder to be coated and a suitable liquid medium to form a slurried mixture. Alternatively, the coating agents may be dissolved in one or more solvents, which optionally may be emulsified and mixed or sprayed on to the powder. Preferably, a single solution of a blend of the two coating agents, each of which may comprise one or more compounds, e.g. compounds of formulae I and II, respectively, is mixed with the powder or powders to be coated, preferably by spraying on to the powder while mixing. However the ingredients are brought together, it is desirable to thoroughly mix the slurry until homogeneity is achieved, with a view to ensuring that the entire surface of each powder particle is wetted.

Any suitable additives that are customary employed in pigment coating processes may be included in the mixture, if desired. For example, various acids, including low molecular weight aqueous organic acids, such as acetic acid, can be used to catalyze the hydrolysis of functionalized silane starting materials. Also, trivalent iron 2-ethylhexanoate or zinc 2-ethylhexanoate can be employed to catalyze reaction of methicone with substrate powder materials. However, in many cases use of such additives or catalysts is not necessary.

If desired, the dried, hybrid-coated powder produced by this process can be pulverized in a mill, for example a jet mill, hammer mill, or other suitable mill.

The resultant alkylpolysiloxane, or alkylpolysiloxane residue, in the hybrid powder coating preferably has a degree of polymerization of from about 5 to about 100, more preferably from about 10 to about 15.

Other processes for producing hybrid coated powders pursuant to the present invention include a two-stage process wherein the powder is first coated with the organometallate and is then coated with the functionalized silicone compound. If desired, the organometallate powder may be dried prior to coating with functionalized silicone compound. Preferably, such intermediate drying step is curtailed or moderated to avoid fully curing the organometallate residues so that the organometallate coated powder particles retain sufficient surface reactivity to effectively bond with the functionalized silicone compound in the second stage of the process. The intermediate drying step is followed by a final drying step, to completely cure the hybrid coating, after the functionalized silicone compound has been applied. Such a two-stage process is contemplated as providing an outer surface of the hybrid coated powder particle which is particularly rich in silicon atoms and accordingly has excellent silicone fluid dispersibility.

Alternatively, the functionalized silicone compound could be applied in a first stage prior to application of the organometallate in a second step, with or without the intermediate drying step. However, the good reactivity of preferred organometallates and their ability to bind effectively with both pigment powder surfaces and many silicone materials renders the application of the organometallate prior to the functionalized silicone compound a particularly attractive two-stage process. Such process is believed preferably to coating with organometallate before silicon because the organometallate may be less resistant to heat. Furthermore, application of the organometallate on to a silicone coated powder substrate is believed advantageous in reacting with residual reactive groups that may remain in the silicone coating, especially on the outer surface thereof.

Optionally each stage may employ a suitable solvent for the respective coating agent, which solvent is sufficiently volatile to be removed by drying.

Preferably, the herein described coating agents are the only reactive coating materials employed. Thus, the reactive coating materials employed in the coating compositions and processes of the present invention preferably consist essentially of an organometallate and a functionalized silicon compound each of which may be one or more of the respective compounds described herein as being useful coating agents.

Coating Structure

Possible chemical structures of the inventive hybrid powder coating are more fully described hereinbelow. Preferred coatings comprise a continuous, complete, coherent coating over the entire outer surface of each powder particle which coating is tenaciously covalently bonded to the powder substrate. Preferably, also the coating has at least one covalent bond to the powder particle substrate for every 100 metal or silicon atoms in the coating agent, more preferably for every 20 such atoms, and still more preferably for at least every 10, or even 5 such atoms.

It will be understood that an alkylpolysiloxane coating agent can provide a residue in the powder coating in the form of a chain of siloxy units. These siloxy units may be terminated with, or interspersed with, organometallate units, may have varying degrees of crosslinking and will have at least some terminal units bonded to the powder substrate. Other terminal units may be capped with organometallate groups or may, in some cases, comprise free hydroxyl groups.

One embodiment of coating according to the invention can have the following structural formula (8), employing titanium as an exemplary metal:

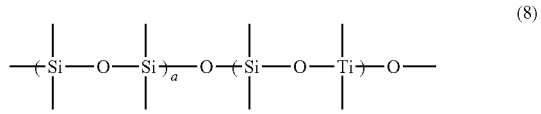

(8)

wherein a is from 1 to 1000, preferably from 1 to 100. The particular value of a will depend upon the starting materials and reaction conditions employed, as will be apparent to those skilled in the art. The structure shown can repeat throughout the coating. The unsatisfied valencies can be occupied by other similar units, some of which may serve as cross links, e.g. through oxygen atoms, powder substrate atoms or groups, or any of the various residual groups described or implicit herein. Valencies not made to other units are preferably satisfied with hydrocarbon or fluorohydrocarbon groups or fatty acid ester groups, as will be apparent from the disclosure herein. Although only one Si—O—Ti group is shown, in some instances multiples of this group may also chain together. However such poly (siloxy-metal) chains are not generally believed to be present to a significant extent in the resultant coatings.

Reaction of the organotitanate coating agent with a silicone as well as the coated powder can provide a structure in the finished coating comprising —Si—O—Ti— units in addition to the conventional polysiloxane backbone units —Si—O—Si—. Thus, such coatings of the present invention have a quite different chemical character from conventional silicone coatings.

Organometallate starting materials having only a single functional entity can be expected to yield coatings wherein single organometallate units are covalently bound to the powder surface and to multifunctional siloxy units that are also covalently bonded to the powder surface, if such siloxy units are present.

If both the organometallate compound and the functionalized silicon compound are unifunctional, then the coating can be expected to consist essentially of a mosaic of single units of each compound which preferably extends continuously, without interruption, over the surface of each cosmetic powder particle. The relative affinities of the coated particles for lipids or silicone fluids will depend upon the relative surface areas the two different units occupy as well as the particular hydrophobic or silicic character of the respective units. In turn, the relative surface areas occupied can be expected to depend upon the molecular sizes and reactivities of the respective starting materials. The respective dispersibilities of the inventive hybrid coated powders in lipids and silicones can be adjusted by varying these parameters as may be determined empirically by the simple experiments described herein.

Organometallate starting materials having two or more functional entities, e.g. two alkoxy groups, can be expected to yield coatings which in addition to the features described in the immediately preceding paragraph include siloxy units coupled to the particle surface through an organometallate unit. Possibly, di-, tri- or polyorganometallate units may bond to the particle surface. However such structures are believed to have only limited stability under most relevant reaction conditions and to fairly readily break down to yield a single organometallate unit bonded to the powder surface.

Of particular interest in the practice of the invention are coated powders formed from difunctional organometallate compounds and difunctional silicon compounds. The resultant coatings can include chains of polysiloxy units coupled to the powder, and possibly also interconnected one to another, by metallate units and may contain —Si—O—M— units wherein valencies not shown are satisfied with substituents present in the starting materials, for example alkyl or ester groups. Such structures are believed desirable in providing durable and cohesive coatings that are tenaciously bonded to the cosmetic powder particles.

While the invention is neither bound nor limited by any particular theory, but only by the appended claims, it is known, for example from DuPont Tyzor® Organic Titanates, Dupont Specialty Chemicals, 11/93, 233629A, that organic titanates are useful for the catalysis and crosslinking of silicones and can catalyze polymerization of various siloxanes for coatings, providing harder surfaces, improved heat and electrical resistance, adhesion, water repellency and resistance to heat and staining. However, that cosmetic powders could obtain improved dispersibility in oils and silicone fluids as a result of the hybrid coatings of the present invention was neither known or suggested. Based on the aforementioned knowledge, it is contemplated that the incorporation of organometallates in the inventive coatings may result in a more complete reaction of compounds such as methyl hydrogen polysiloxane or methyl hydrogen polysiloxane and dimethylpolysiloxane copolymer with pigment, e.g. more complete reaction of their Si—H groups, lowering the potential for the generation of hydrogen over time, for example during storage, by the coated pigment.

Furthermore, complete, or essentially complete, reaction of functionalized silicon compounds such as methyl hydrogen silicone may be effective in reducing or eliminating problems of color shift, possibly by reducing long term surface reactivity and resultant particle agglomeration.

It will be understood that each of the organometallate and functionalized silicon starting materials may itself constitute a mixture of materials of various functionality, with the resulting coatings having a blend of the above-described structures.

It will also be understood that whereas the structures of the novel powder coatings of this invention, and possibly also of some of the starting materials, are described in terms of covalent bonds, such descriptions may be idealized and the actual chemical structures may and probably will display some characteristics of ionic, hydrogen and van der Waals bonding, without departing from the teachings herein.

The invention also includes a lipid- and silicone-dispersible coated cosmetic powder comprising cosmetic powder particles and a hydrophobic coating on the cosmetic powder particles, the hydrophobic coating conferring lipid and silicone dispersibility on the cosmetic powder particles and comprising:

a) cosmetically stable hydrophobic organometallate units of formula $(R^6)_g M_1$-O— wherein:

$M_1$ is a metal capable of forming cosmetically stable organometallate compounds of the structure shown, including any of the metals M;

a equals the valence state of metal $M_1$ minus 1 or minus 2, wherein, in the case of the latter alternative, the available valence of metal $M_1$ is covalently bonded to another $M_1$ atom or to a coating material oxygen atom;

$R^6$ is a hydrophobic organic moiety including a cosmetically stable covalent bond to metal M or, when a is greater than 1, to an oxygen atom with an available valence and wherein multiple $R^6$s, if present, may be the same or different; and b) cosmetically stable siloxy units of formula D_$R^7$_$R^8$_Si—O—, "Formula (9)" hereinafter, wherein:

D is an oxygen atom with an available valence or a hydrophobic organic moiety including a cosmetically stable covalent bond to the silicon atom; and $R^7$ and $R^8$ may be the same or different and are each a hydrophobic organic moiety including a cosmetically stable covalent bond to the silicon atom;

wherein the hydrophobic coating is covalently bonded to the cosmetic powder by satisfaction of available oxygen valencies in the organometallate and siloxy units.

Some preferred embodiments of $R^7$ and $R^8$ include optionally saturated hydrocarbon or fluorohydrocarbon groups having from 1 to 30 carbon atoms and other such groups as will be apparent from the disclosure herein. Other possible groups for D include the same groups as for $R^7$.

The organometallate units in Formula (9) include units having two available oxygen valencies, at least one of the two organometallate unit available oxygen valencies being satisfied by a covalent bond to one of the siloxy units or to another organometallate unit, and the hydrophobic coating can include siloxy units bonded to the powder through organometallate units.

The siloxy units in Formula (9) include units having two available oxygen valencies at least one of the two siloxy unit available oxygen valencies being satisfied by a covalent bond to one of the siloxy units or to another organometallate unit and the hydrophobic coating can include polysiloxy units.

Both the organometallate units and the siloxy units in Formula 7 can include units having two available oxygen valencies and the hydrophobic coating includes poly siloxy units bonded to the powder through organometallate units.

The coating can comprise a stoichiometric proportion of organometallate units to siloxy units of from about 0.05:1 to about 10:1, preferably about 0.4:1 to about 3:1.

Some embodiments of the invention, and of making and using the invention, are described, without limitation, in the following examples which in conjunction with the foregoing description include the best mode contemplated of carrying out the invention.

COMPARATIVE EXAMPLE A: ISOPROPYL TITANIUM TRIISOSTEARATE-COATED $TIO_2$ 98 g of titanium dioxide powder, product code X200 from Kemira Corporation, are added to a blender. 5.9 g of a 34% wt/wt solution of isopropyl titanium triisostearate (referenced "ITT" hereinafter) in ISOPAR C isoparaffinic fluid are sprayed on the titanium dioxide powder in the blender under agitation. The slurry mixture is thoroughly blended, transferred to a tray and dried at 110° C. for 4 hours. It is then cooled down to room temperature and pulverized.

COMPARATIVE EXAMPLE B: TRIETHOXY OCTYLSILANE-COATED $TIO_2$

Comparative Example A is repeated employing the same quantity of triethoxy octylsilane in place of isopropyl titanium triisostearate. The coated powders obtained from Comparative Examples A and B are used for comparison in tests such as those described hereinbelow.

COMPARATIVE EXAMPLES C-D: COATED RED IRON OXIDE

Comparative Examples A and B are repeated employing the same quantity of red iron oxide from Sun Chemical Corporation in place of the titanium dioxide powder to yield ITT-coated red iron oxide (Comparative Example C) and triethoxy octylsilane-coated red iron oxide (Comparative Example D). The resultant coated powders are used for comparison in tests such as those described hereinbelow.

EXAMPLE 1: HYBRID COATING OF $TIO_2$ 98 g of titanium dioxide powder, product code X200 from Kemira Corporation, are added to a blender. 5.9 g of a 34% wt/wt solution of a hybrid coating mixture (about 2% by weight of the coated product) comprising equal parts of isopropyl titanium triisostearate and triethoxy octylsilane, referenced "the hybrid coating mixture" hereinafter, are sprayed on the titanium dioxide powder under agitation. The mixture is thoroughly blended, transferred to a tray and dried at 110° C. for 4 hours. It is then cooled down to room temperature and pulverized to provide hybrid titanate-silicone-coated titanium dioxide powder of a desired particle size.

EXAMPLE 2: HYBRID COATING OF RED IRON OXIDE

Example 1 is repeated using 98 g of red iron oxide powder from Sun Chemical Corporation in place of the titanium dioxide powder to yield titanate-silicone-coated red iron oxide powder.

EXAMPLE 3: HYBRID COATING OF YELLOW IRON OXIDE AND BLACK IRON OXIDE

Example 1 is repeated using 98 g of yellow iron oxide powder or black iron oxide powder in place of the titanium dioxide powder to yield titanate-silicone-coated yellow or black iron oxide powder.

EXAMPLE 4: HYBRID COATING OF BARIUM LAKE

Example 1 is repeated using 95 g of K 7096 D&C Red 6 barium lake from LCW in place of the titanium dioxide powder to yield titanate-silicone-coated barium lake powder.

EXAMPLE 5: HYBRID COATING OF MICA

Example 1 is repeated using a similar quantity of mica in place of the titanium dioxide powder to yield titanate-silicone-coated mica powder.

EXAMPLE 6: HYBRID COATING OF SILICA

Example 1 is repeated using a similar quantity of silica in place of the titanium dioxide powder to yield titanate-silicone-coated silica powder.

Each of the powders coated with hybrid material produced by the methods of Examples 1-6 shows good water repellency, has a smooth feel and good adhesion to the skin. After mixing and shaking with water, each hybrid-coated powder floats well and the water soon becomes a similar.

The properties of the hybrid coated powder products obtainable by the methods of Examples 1-5 can be determined by various tests, as known to those skilled in the art, some of which are described below:

Test 1: Hydrophobicity

In a quick and simple test to determine hydrophobicity, 1 g of pigment powder is shaken vigorously 10 times in a glass container in 50 ml of water. The sample is allowed to stand for one minute and the clarity of the water is observed. Results obtainable are shown in Table 1 below.

TABLE 1

| Hydrophobicity | | | |
|---|---|---|---|
| | Example A | Example B | Example 1 |
| Water phase | Cloudy | Clear | Clear |

The treatment of titanium dioxide pursuant to Comparative Example A, employing isopropyl titanium triisostearate, provides a product which is significantly less hydrophobic than is obtainable with Comparative Example B, employing a silane, triethoxy octylsilane. Example 1, wherein titanium dioxide is coated with a hybrid composition according to the present invention, exhibits comparable hydrophobicity to the silane treatment of Comparative Example B being also significantly better than isopropyl titanium triisostearate, Comparative Example A.

Test 2: pH Stability 0.5 g of fine coated pigment powder are carefully deposited onto the surface of 50 g of distilled water having the indicated pH in a 100 ml beaker. The time when the pigment powder starts to break the surface and sink into the water is observed. Results obtainable are shown in Table 2 below.

TABLE 2

| pH Stability | | | |
|---|---|---|---|
| | Time when particles begin to sink | | |
| pH | Example A | Example B | Example 1 |
| pH4 | 3 hr. 20 min. | >2 weeks | >2 weeks |
| pH5 | >3 days | | |
| pH6 | >3 days | | |
| pH7 | >5 days | | |
| pH8 | >7 days | | |
| pH9 | >7 days | | |

The pigment treated pursuant to Comparative Example A, isopropyl titanium triisostearate coated, shows loss of hydrophobicity at all tested alkaline, neutral and acid pHs after 7 days, i.e. before 8 days. In the case of acid pHs the loss becomes apparent after about 3 days. In contrast, both the silane-coated product of Comparative Example B and the hybrid-coated product of Example 1 of the invention are stable for more than two weeks at all pHs in the test. Both products have a hydrophobicity which is significantly more resistant to acid pHs than is that of pigment coated with isopropyl titanium triisostearate. Thus, the hybrid coating of Example 1 displays excellent stability over a wide pH range.

Test 3: Dispersibility in Hydrophobic Fluids

Various proportions of pigment powder, as shown in Table 3 below, are blended into two different hydrophobic fluids, namely mineral oil and a cyclomethicone product, for example GE Silicones product number SF1528 which is described as a water-in-oil silicone emulsifier comprising a 10% silicone polyether copolymer dispersed in cyclopentasiloxane (a cyclomethicone). The viscosities of the resultant dispersions are determined by known methods and results obtainable are shown in Table 3 below from which it may be seen that, surprisingly the hybrid coated pigments of the invention have good dispersibility in both oils and silicone fluids.

TABLE 3

| Dispersibility in Hydrophobic Fluids | | | | |
|---|---|---|---|---|
| | In Mineral Oil | | In Cyclomethicone | |
| Pigment Tested | Solids % | Viscosity | Solids % | Viscosity |
| Titanium dioxide | | | | |
| Uncoated | 40 | 346,000 | 73 | N/A |
| Comparative Example A: ITT*-coated | 80 | 108,400 | 75 | 1,316,000 |
| Comparative Example B: Silane-coated | 80 | 698,000 | 75 | 505,000 |
| Invention Example 1: Hybrid-coated | 80 | 286,000 | 75 | 761,000 |
| Red Iron Oxide (Cosmetic russet) | | | | |
| Uncoated | 50 | N/A | 60 | 1,312,000 |
| Comparative Example C: ITT*-coated | 75 | 121,200 | 73 | 824,000 |
| Comparative Example D: Silane-coated | 75 | 627,000 | 73 | 292,000 |
| Invention Example 2: Hybrid-coated | 75 | 126,400 | 73 | 488,000 |

*ITT = isopropyl titanium triisostearate

The uncoated pigments are difficult to disperse in either liquid. Even at the lower solids loadings indicated the resultant dispersion is either very viscous or the viscosity cannot readily be measured. The inventive hybrid coating, Examples 1 and 2, improves the dispersibility of both titanium dioxide and red iron oxide significantly over the uncoated pigment powders.

Furthermore, the hybrid coated pigment powders of the invention exhibit significant lipophilicity as shown by a marked improvement in the dispersibility, of both pigment powders in oils, e.g. mineral oil, as is indicated by the relatively lower viscosities in such a medium, that are shown in Table 3. In the case of red iron oxide, the hybrid coating of Example 2 is almost as effective as the isopropyl titanium triisostearate coating of Comparative Example C.

In contrast, the silane-coated pigments of Comparative Examples B and D which disperse well in the cyclomethicone fluid, yield highly viscous dispersions in mineral oil, indicating poor lipophilicity.

Results for the dispersibility of the pigments in cyclomethicone show that the hybrid-coated pigment of Examples 1 and 2 is has good dispersibility in silicone fluids such as the above-described cyclomethicone material, showing a substantial reduction in viscosity as compared with the isopropyl titanium triisostearate treated pigments of Comparative Examples A and C or the uncoated pigments, or compatible provides a as effectively as silane coating.

Test C shows that the inventive hybrid coating can provide a combination of desirable properties which are exhibited individually by isopropyl titanium triisostearate and silane coatings, namely both good lipophilicity and good silicone fluid dispersibility.

Test 4: Stability During Grinding

To determine the stability of the pigment coating during grinding, the coated pigments are dispersed in a suitable cosmetic pigment emulsifier using a mixer and are ground in a mill. Employing an emulsifier supplied by Goldschmidt Chemical Corp., Hopewell, Va. under the trademark ABIL® WE 09, the results described in Table 4, below are obtainable. The ABIL® WE 09 emulsifier is described as comprising a mixture of (polyglyceryl-4 isostearate, cetyl dimethicone copolyol and hexyl laurate.

TABLE 4

Grinding Stability

| Dispersion Formula | | Odor |
|---|---|---|
| 70 parts ITT-coated TiO$_2$ (Comparative Example A) | 30 parts emulsifier | Slight waxy odor |
| 70 parts hybrid-coated TiO$_2$ (Invention Example 1) | 30 parts emulsifier | Little, if any odor. |

The hybrid coating of Example 1 has a dispersibility in the emulsifier, for example Abil® WE 09 emulsifier, which is comparable with that of the isopropyl titanium triisostearate coating, yet generates little or no odor, an important consideration for the aesthetics of finished consumer products.

COMPARATIVE EXAMPLE E
METHICONE-COATED TIO$_2$ 96 g of ultrafine titanium dioxide powder, product code A0189 from ISK Co., Japan, average particle size no greater than 100 nm, are added to a blender. 11.76 g of a solution of methicone (34% wt/wt) product code KF-9901 from Shin-Etsu Chemical Co. Ltd. in ISOPAR C isoparaffinic fluid are sprayed on the powder under agitation. The mixture is well blended, transferred to a tray and dried at 110° C. for 4 hours. It is then cooled down to room temperature and pulverized to a desired particle size. The methicone-coated titanium dioxide powder obtained shows poor hydrophobicity. After mixing and shaking with water, the powder disperses into water and the water remains cloudy indicating poor hydrophobicity.

COMPARATIVE EXAMPLE F
METHICONE-COATED ZnO

Comparative Example E is repeated with the difference that a similar quantity of ultrafine zinc oxide powder, average particle size no greater than 100 nm is employed in place of the titanium dioxide powder. A similar result is obtained.

EXAMPLE 7: HYBRID COATING OF TIO$_2$ EMPLOYING METHICONE

Comparative Example E is repeated except that 11.76 g of a solution of a mixture of ITT (17% wt/wt based on the solution) and methicone (17% wt/wt based on the solution) in ISOPAR C isoparaffinic fluid is employed in place of the solution of methicone. The hybrid titanate-methicone-coated titanium dioxide powder obtained shows excellent hydrophobicity. After mixing and shaking with water, the powder floats well and the water soon becomes clear, indicating excellent hydrophobicity.

Comparing Example 7 with Comparative Example E shows that coating of ultrafine titanium dioxide with the inventive hybrid titanate-methicone composition yields a product with surprisingly superior hydrophobicity to that of a conventionally treated methicone coated product. In addition, while the invention is not limited by any particular theory, it is hypothesized that use of an organotitanate, or other organometallate pursuant to the invention may result in more complete reaction of the methicone —Si—H groups, relieving the problem of spontaneous hydrogen generation in storage to which methicone-containing products are subject. In addition, methicone-induced color shift during storage is expected to be inhibited.

EXAMPLE 8: HYBRID COATING OF ZNO EMPLOYING METHICONE

Example 7 is repeated with the difference that a similar quantity of ultrafine zinc oxide powder, average particle size no greater than 100 nm, is employed in place of the titanium dioxide powder. A similar result is obtained.

EXAMPLE 9: OIL-IN-WATER LIQUID MAKEUP

The following ingredients are employed in the proportions indicated to prepare an oil-in-water liquid makeup:

| | % |
|---|---|
| Part A | |
| Lanolin Alcohol (and) Mineral Oil | 11.50 |
| Cetyl esters | 3.20 |
| Stearic Acid | 3.50 |
| Glyceryl Monostearate | 1.80 |
| Talc | 2.00 |
| Titanium dioxide (w/hybrid coating) | 4.00 |
| Yellow iron oxide (w/hybrid coating) | 1.00 |
| Red iron oxide (w/hybrid coating) | 0.40 |
| Black iron oxide (w/hybrid coating) | 0.15 |
| Part B | |
| Propylene glycol | 12.00 |
| Triethanolamine | 1.00 |
| PE 20 Sorbitan Monolaurate | 0.65 |
| Magnesium Aluminum Silicate | 1.00 |
| Carboxymethyl Cellulose | 0.30 |
| Deionized Water | 57.20 |
| Preservatives and Fragrance | QS |

The titanium dioxide and iron oxide pigments are provided with hybrid coatings pursuant to the invention, for example as described in Examples 1-3. The ingredients of Part A are combined, in the order shown, while thoroughly mixing each component until homogenous before adding the next ingredient. The mixture is heated to 60° C. The ingredients of Part B are combined in a separate vessel. The mixture of Part B ingredients is slowly added to the Part A mixture with good mixing and the product is poured into suitable containers. A high quality product is obtained.

EXAMPLE 10: LIQUID COMPACT FOUNDATION (HOT POUR)

The following ingredients are employed in the proportions indicated to prepare a hot pour liquid compact foundation:

|  | % |
| --- | --- |
| Part A | |
| Titanium dioxide (w/hybrid coating) | 26.76 |
| Red iron oxide (w/hybrid coating) | 0.54 |
| Yellow iron oxide (w/hybrid coating) | 0.54 |
| Black iron oxide (w/hybrid coating) | 0.16 |
| Mica (w/hybrid coating) | 10.00 |
| Silica (spherical) (w/hybrid coating) | 2.00 |
| Part B | |
| Squalene | 10.00 |
| Dimethicone (5 cst) | 17.00 |
| Octyl hydroxystearate | 7.00 |
| Polyglyceryl-3 diisostearate | 3.00 |
| Microcrystalline wax | 7.00 |
| Octyl palmitate | 7.00 |
| Carnauba wax | 1.00 |
| Part C | |
| Nylon -12 | 8.00 |

Each of the pigment materials in Part A is provided with a hybrid coating pursuant to the invention, for example as described in Examples 1-5. The ingredients of Part A are micronized until the color is fully developed. The ingredients of Part B are heated, with stirring, to about 90-93° C. (195-200° F.). Continue to stir for ½ hour. Add Part A to Part B and mix until homogeneous. Cool to about 82° C. (180° F.). The Part C ingredient and mixing is continued until the mixture is homogeneous and is then poured into pans at about 74-77° C. (165-170)° F. A high quality product is obtained.

EXAMPLE 11: LIPSTICK

The following ingredients are employed in the proportions indicated to prepare a hot pour liquid compact foundation:

| Ingredient | % |
| --- | --- |
| Candelilla Wax | 6.00 |
| Carnauba Wax | 3.00 |
| Ozokerite | 4.00 |
| Paraffin Wax | 2.00 |
| Yellow Beeswax | 6.00 |
| Lanolin Alcohol | 6.00 |
| Oleyl Alcohol, | 10.00 |
| BHA | 0.20 |
| Castor Oil | 43.25 |
| D&C Red No. 6 Barium Lake (w/hybrid coating) | 2.50 |
| D&C Red No. 7 Calcium Lake (w/hybrid coating) | 2.50 |
| Iron Oxides (w/hybrid coating) | 1.00 |
| FD&C Blue No. 1 | 0.80 |
| Perfume | 0.75 |
| Titanium Dioxide (and) Mica (w/hybrid coating) | 10.00 |

Each of the pigment materials is provided with a hybrid coating pursuant to the invention, for example as described in Examples 1-8. Castor oil is placed in the main mixer and heated to 80° C. using a steam pan. The coated lakes, coated iron oxides and the dyes are slowly mixed into the castor oil using a Lightnin' mixer under high speed for 30-60 minutes. The candelilla wax, carnauba wax, beeswax, ozokerite paraffin wax oleyl alcohol and lanolin alcohol are all preheated and melted together at 80-85° C. using a steam pan and added to the castor oil, pigment and dye mixture. Mixing is continued throughout the addition of these ingredients.

The perfume is then added and mixing is continued until the mixture is homogeneous. The hybrid coated titanium dioxide and mica, pigments providing pearlescence, are then added and mixing continues until the product is uniform.

The lipstick is then cooled and shaped in conventional manner. A high quality product with excellent coverage is obtained.

The powder coating agents, methods and products of the invention enable a wide range of cosmetics powders to be coated with the same treatment and provide a broad spectrum of dispersibility properties enabling the coated powders to be utilized in a diversity of media including aqueous, lipid or oily media and silicone fluids. A particular benefit of the invention is that a diversity of different powder ingredients in a multiphase cosmetic formulation may receive the same hydrophobizing treatment and may in some cases be mixed together and coated in a single process.

In summary, the hybrid coating of the invention can provide, in preferred embodiments, in a single coating, many of the benefits that are known to be obtainable separately with either an ITT coating or a silane coating. The inventive hybrid coatings can improve the dispersibility of pigments and other powders in oils nearly as effectively as does an ITT coating and in cyclomethicone nearly as effectively as does a silane coating.

INDUSTRIAL APPLICABILITY

The present invention is particularly suitable for application in the cosmetics industry providing novel and improved coated powder ingredients, processes and consumer products such as makeups, foundations, lipsticks and the like. In addition, the novel hybrid coated powders of the invention, coating compositions and processes and end product formulations containing the coated powders may be useful in other industries, for example, in the paints and coatings industries and the plastics, rubber, adhesives, tile and other industries where the novel properties of the inventive materials and processes may be advantageous.

Other possible fields of application will be known or apparent to those skilled in the art from the disclosures herein. It will also be understood that the particular materials selected for such applications in other industries may not be required to meet accepted criteria for cosmetic compatibility, enabling the skilled worker to choose from among a broad range of possible ingredients the particular ingredients to use to practice the invention.

Disclosures Incorporated

The entire disclosure of each and every United States patent and patent application, each foreign and international patent publication, of each other publication and of each unpublished patent application that is referenced in this specification or elsewhere in this patent application, is hereby incorporated herein, in its entirety, by the respective specific reference that has been made thereto.

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

The invention claimed is:

1. A coating process for making a hydrophobic coated cosmetic powder, wherein the coating process comprises:
selecting a cosmetic powder having a mean particle size of 0.01 to 20.0 µm, to be hydrophobized with a hybrid coating comprising an organotitanate coating agent and a functionalized silicone coating agent;
dissolving the organotitanate coating agent and the functionalized silicone coating agent in a volatile solvent to produce a solution of the organotitanate coating agent and the functionalized silicone coating agent;
mixing the solution of the organotitanate coating agent and the functionalized silicone coating agent into or spraying the solution of the organotitanate coating agent and the functionalized silicone coating agent on the cosmetic powder to produce a silicone and organotitanate treated cosmetic powder; and
heating the silicone and organotitanate treated cosmetic powder at an elevated temperature, in a range from 60° C. to about 130° C.; and
allowing the silicone and organotitanate treated cosmetic powder to dry, resulting in substantial removal of the solvent,
whereby the organotitanate coating agent and the functionalized silicone coating agent form a hybrid coating which is covalently bonded to the cosmetic powder, and wherein said hybrid coating is applied in an amount resulting in the coating comprising 1.0 to 10.0 percent by weight of the hybrid-coated cosmetic powder.

2. The coating process of claim 1, wherein the cosmetic powder is hydrophobized with the hybrid coating and hammer milled.

3. The coating process of claim 1, wherein the cosmetic powder is hydrophobized with the hybrid coating and jet milled.

4. The coating process of claim 1, wherein the organotitanate and functionalized silicone coating agents are dissolved in isopar C.

5. The coating process of claim 4, wherein the organotitanate coating agent is a liquid monoalkoxy ($C_1$ to $C_{20}$) isostearoyl titanate and the functionalized silicone coating agent is selected from the group consisting of any suitable functionalized silane, functionalized polysiloxane, and functionalized silicon.

6. The coating process of claim 5, wherein the liquid monoalkoxy ($C_1$ to $C_{20}$) isostearoyl titanate coating agent is isopropyl triisostearoyl titanate.

7. The coating process of claim 6, wherein the cosmetic powder is an ultrafine titanium dioxide, the organotitanate coating agent is isopropyl triisostearoyl titanate and the functionalized polysiloxane coating agent contains reactive Si—H bonds.

8. The coating process of claim 7, wherein the cosmetic powder is an ultrafine titanium dioxide of an average particle size less than 100 nm, wherein said hybrid coating is contained at an amount of 4.0 percent by weight to the hybrid-coated ultrafine titanium dioxide.

9. The coating process of claim 6, wherein the cosmetic powder is zinc oxide, the organotitanate coating agent is isopropyl triisostearoyl titanate and the functionalized polysiloxane coating agent contains reactive Si—H bonds.

10. The coating process of claim 9, wherein the cosmetic powder is zinc oxide of an average particle size less than 100 nm, and wherein said hybrid coating is contained at an amount of 4.0 percent by weight to the hybrid-coated zinc oxide.

11. The coating process of claim 6, wherein the functionalized silane coating agent is triethoxy octylsilane.

12. The coating process of claim 6, wherein the functionalized polysiloxane is methyl hydrogen polysiloxane or dimethylpolysiloxane copolymer.

13. The coating process of claim 6, wherein the functionalized polysiloxane coating agent is a branched silicone.

14. The coating process of claim 13, wherein the branched silicone is triethoxysilylethylpolydimethylsiloxyethyl dimethicone.

15. The coating process of claim 4, further comprising:
dispersing the hybrid-coated cosmetic powder in a cosmetic pigment emulsifier using a mixer to create a dispersion; and
grinding the dispersion in a mill.

16. A method as in claim 15, wherein the volatile solvent liquid is removed from the hybrid-coated cosmetic powder.

17. The coating process of claim 1, wherein said hybrid coating comprises about 1.0 to about 5.0 percent by weight of the hybrid-coated cosmetic powder.

18. The coating process of claim 17, wherein said hybrid coating comprises about two percent by weight of the hybrid-coated cosmetic powder.

19. The coating process of claim 1, wherein the cosmetic powder is selected from the group consisting of titanium dioxide, zinc oxide, and iron oxides.

20. The coating process of claim 1, wherein the cosmetic powder is an organic coloring pigment.

21. A process as in claim 1, wherein said mixing or spraying of the solution of the organotitanate coating agent and the functionalized silicone coating agent on the cosmetic powder is done under agitation to produce the treated cosmetic powder.

22. The process of claim 1 wherein the coating agents are dissolved in a volatile solvent or solvents and mixed with or sprayed on the cosmetic powder separately.

23. A coating process for coating a hydrophobic cosmetic powder, comprising:
selecting a cosmetic powder having a mean particle size of 0.01 to 20.0 µm to be hydrophobized with a hybrid coating comprising an organotitanate coating agent and a functionalized silicone coating agent;
dissolving the organotitanate coating agent in a volatile solvent to produce a titanate solution of the organotitanate coating agent;
dissolving the functionalized silicone coating agent in a volatile solvent to produce a solution of the functionalized silicone coating agent;
mixing the silicone solution with the cosmetic powder or spraying the silicone solution onto the cosmetic powder;
mixing the titanate solution with or spraying the titanate solution onto the cosmetic powder, after mixing the silicone solution with the cosmetic powder or spraying the silicone solution onto the cosmetic powder, to produce a silicone and organotitanate treated cosmetic powder; and
heating the silicone and organotitanate treated cosmetic powder at an elevated temperature, in a range from 60° C. to about 130° C.; and allowing the silicone and organotitanate treated cosmetic powder to dry resulting in substantial removal of the solvent, whereby the organotitanate coating agent and the functionalized silicone coating agent form a hybrid coating which is covalently bonded to the cosmetic powder, and wherein said coating solution is applied in an amount sufficient to result in said hybrid coating comprising 1.0 to 10.0 percent by weight of the hydrophobized cosmetic powder.

24. A method as in claim 23, wherein the volatile solvent liquid is removed from the silicone and organotitanate treated cosmetic powder.

25. A method as in claim 23, wherein mixing the titanate-silicone solution with or spraying the titanate-silicone solution onto the cosmetic powder results in the creation of a pigment mixture, and further comprising removing the liquid component from the pigment mixture to produce a silicone and organotitanate treated cosmetic powder.

26. A method as in claim 23, wherein the cosmetic powder is selected from the group consisting of titanium dioxide, red iron oxide, yellow iron oxide, black iron oxide, barium lake, mica and silica.

27. A coating process for making a hydrophobic cosmetic powder, wherein the coating process comprises:
selecting a cosmetic powder, from the group consisting of titanium dioxide, red iron oxide, yellow iron oxide, black iron oxide, barium lake, mica and silica with a mean particle size of 0.01 to 20.0 µm, to be hydrophobized with a hybrid coating comprising an organotitanate coating agent and a functionalized silicone coating agent, said hybrid coating comprising 1.0 to 10.0 percent by weight of the hydrophobized cosmetic powder,
dissolving the organotitanate coating agent in a volatile solvent to produce a titanate solution of the organotitanate coating agent;
dissolving the functionalized silicone coating agent in a volatile solvent to produce a solution of the functionalized silicone coating agent;
mixing the solution of the functionalized silicone coating agent with the cosmetic powder or spraying the silicone solution onto the cosmetic powder;
mixing the titanate solution with or spraying the titanate solution onto the cosmetic powder, after mixing the silicone solution with the cosmetic powder or spraying the silicone solution onto the cosmetic powder, to produce a silicone and organotitanate treated cosmetic powder; and
heating the silicone and organotitanate treated cosmetic powder at an elevated temperature, in a range from 60° C. to about 130° C., allowing the silicone and organotitanate treated cosmetic powder to dry resulting in substantial removal of the solvent,
whereby the organotitanate coating agent and the functionalized silicone coating agent form a hybrid coating which is covalently bonded to the cosmetic powder.

28. A coating process for making a hydrophobic coated cosmetic powder, wherein the coating process comprises:
selecting a cosmetic powder, substantially consisting of material selected from the group consisting of titanium dioxide, red iron oxide, yellow iron oxide, black iron oxide, barium lake, mica and silica, with a mean particle size of 0.01 to 20.0 µm to be hydrophobized with a hybrid coating comprising an organotitanate coating agent and a functionalized silicone coating agent;
forming a mixture of the cosmetic powder by combining the cosmetic powder with a liquid medium;
dissolving the organotitanate coating agent in a volatile solvent to produce a titanate solution of the organotitanate coating agent;
dissolving the functionalized silicone coating agent in a volatile solvent to produce a solution of the functionalized silicone coating agent;
applying the solution of organotitanate coating agent to the cosmetic powder in the mixture under mixing or agitation or the equivalent;
applying the solution of functionalized silicone coating to the cosmetic powder in the mixture under mixing or agitation or the equivalent to create a mixture of the silicone and organotitanate treated cosmetic powder;
removing the solvent from the mixture of the silicone and organotitanate treated cosmetic powder to create a silicone and organotitanate treated cosmetic powder; and
heating the silicone and organotitanate treated cosmetic powder at an elevated temperature, in a range from 60° C. to about 130° C., allowing the silicone and organotitanate treated cosmetic powder to dry resulting in substantial removal of the solvent,
whereby the organotitanate coating agent and the functionalized silicone coating agent form a hybrid coating which is covalently bonded to the cosmetic powder, and wherein said hybrid coating is applied to result in the coating comprising 1.0 to 10.0 percent by weight of the hydrophobized cosmetic powder.

29. A coating process as in claim 28, wherein the organotitanate coating agent and the functionalized silicone coating agent are both dissolved in the same solvent to form the solutions of the coating agents.

30. The process of claim 29 wherein the organio-titanate coating agent is dissolved in volatile solvent(s) and mixed with or sprayed onto the cosmetic powder before the functionalized silicone is mixed with or sprayed on the cosmetic powder.

31. The process of claim 29 wherein the functionalized silicone is dissolved in volatile solvent(s) and mixed with or sprayed onto the cosmetic powder before the organo-titanate coating agent is mixed with or sprayed on the cosmetic powder.

* * * * *